United States Patent
Tauber et al.

(10) Patent No.: US 8,337,413 B2
(45) Date of Patent: Dec. 25, 2012

(54) SENSOR SYSTEM FOR MEASURING, TRANSMITTING, PROCESSING AND DISPLAYING A BRAIN PARAMETER

(75) Inventors: Karsten Tauber, Bayreuth (DE); Christian Von Falkenhausen, Meckenheim (DE); Gerd Kunze, Zwönitz (DE); Karl-Heinz Göhler, Zwönitz (DE)

(73) Assignee: Raumedic AG, Münchberg (DE)

( * ) Notice: Subject to any disclaimer, the term of this patent is extended or adjusted under 35 U.S.C. 154(b) by 181 days.

(21) Appl. No.: 12/680,721

(22) PCT Filed: Sep. 11, 2008

(86) PCT No.: PCT/EP2008/007442
§ 371 (c)(1),
(2), (4) Date: Mar. 29, 2010

(87) PCT Pub. No.: WO2009/043431
PCT Pub. Date: Apr. 9, 2009

(65) Prior Publication Data
US 2010/0217108 A1    Aug. 26, 2010

(30) Foreign Application Priority Data

Sep. 28, 2007   (DE) .......................... 10 2007 046 694

(51) Int. Cl.
*A61B 5/00* (2006.01)
*A61B 5/03* (2006.01)

(52) U.S. Cl. ........... 600/561; 600/546; 607/62; 607/139
(58) Field of Classification Search .................. 600/546, 600/561; 607/62, 139
See application file for complete search history.

(56) References Cited

U.S. PATENT DOCUMENTS

| | | | |
|---|---|---|---|
| 4,519,401 A | 5/1985 | Ko et al. | |
| 4,676,255 A | 6/1987 | Cosman | |
| 5,807,397 A | 9/1998 | Barreras | |
| 5,873,840 A | 2/1999 | Neff | |
| 6,016,449 A * | 1/2000 | Fischell et al. | 607/45 |
| 6,248,126 B1 * | 6/2001 | Lesser et al. | 607/113 |

(Continued)

FOREIGN PATENT DOCUMENTS

DE   19705474 A1   8/1998

(Continued)

OTHER PUBLICATIONS

Examination report in corresponding German priority application No. 10 2007 046 694.5.

*Primary Examiner* — Sean Dougherty
(74) *Attorney, Agent, or Firm* — Browdy and Neimark, PLLC

(57) ABSTRACT

A sensor system is used for measuring, transmitting, processing and displaying a brain parameter. The sensor system has at least one implantable brain parameter sensor with a wireless transmission unit for measuring the brain parameter. At least one receiving unit with an antenna is in wireless signal connection with the latter. At least one data read module is in signal connection with the antenna and a data processing and display device is in turn in signal connection with said data read module. The sensor system also has a head cap or a head hood, on which the receiving unit is fixed to predetermine a relative position relative to the transmitting unit. A sensor system is the result, the use of which remains comfortable for the patient even over a relatively long measuring period.

10 Claims, 3 Drawing Sheets

U.S. PATENT DOCUMENTS

| | | | |
|---|---|---|---|
| 6,292,698 | B1 | 9/2001 | Duffin et al. |
| 6,354,299 | B1* | 3/2002 | Fischell et al. ............... 128/899 |
| 6,468,219 | B1 | 10/2002 | Njemanze |
| 6,708,051 | B1* | 3/2004 | Durousseau ................ 600/383 |
| 7,068,225 | B2* | 6/2006 | Schantz ................ 343/700 MS |
| 7,191,013 | B1 | 3/2007 | Miranda et al. |
| 7,647,097 | B2* | 1/2010 | Flaherty et al. ............... 600/544 |
| 8,024,049 | B1* | 9/2011 | Gilson et al. ................ 607/139 |
| 2002/0099412 | A1* | 7/2002 | Fischell et al. ..................... 607/3 |
| 2003/0023146 | A1 | 1/2003 | Shusterman |
| 2005/0090756 | A1 | 4/2005 | Wolf et al. |
| 2005/0107716 | A1 | 5/2005 | Eaton et al. |
| 2005/0137652 | A1 | 6/2005 | Cauller et al. |
| 2005/0283203 | A1* | 12/2005 | Flaherty et al. ............... 607/48 |
| 2006/0025704 | A1 | 2/2006 | Stendel et al. |
| 2008/0161659 | A1* | 7/2008 | Reichenberger et al. ..... 600/301 |
| 2008/0262319 | A1* | 10/2008 | Reichenberger et al. ..... 600/300 |
| 2008/0293446 | A1* | 11/2008 | Rofougaran ............... 455/552.1 |
| 2009/0112278 | A1* | 4/2009 | Wingeier et al. ................ 607/45 |
| 2010/0018295 | A1* | 1/2010 | Kunze ......................... 73/64.45 |

FOREIGN PATENT DOCUMENTS

| | | | |
|---|---|---|---|
| DE | 10215115 | A1 | 10/2003 |
| DE | 69634689 | T2 | 2/2006 |
| DE | 69634810 | T2 | 5/2006 |
| DE | 102005008454 | A1 * | 8/2006 |
| DE | 102005008627 | A1 * | 8/2006 |
| DE | 202007002592 | U1 | 4/2007 |
| DE | 102007046694 | * | 4/2009 |
| EP | 1312302 | A2 | 5/2003 |
| WO | 2004023993 | A1 | 3/2004 |
| WO | WO 2004023993 | A1 * | 3/2004 |
| WO | WO 2006089606 | A1 * | 8/2006 |
| WO | WO 2006089607 | A1 * | 8/2006 |

* cited by examiner

SENSOR SYSTEM FOR MEASURING, TRANSMITTING, PROCESSING AND DISPLAYING A BRAIN PARAMETER

FIELD OF THE INVENTION

The invention relates to a sensor system for measuring, transmitting, processing and displaying a brain parameter with at least one implantable brain parameter sensor with a wireless transmission unit for measuring the brain parameter, with at least one receiving unit with an antenna, which is in wireless signal connection with the transmission unit, with at least one data read module, which is in signal connection with the antenna by means of a signal connection, and with at least one data processing and display device, which is in signal connection with the data read module.

The invention also relates to a head cap or a head hood, respectively (Kopfhaube), for a sensor system of this type.

BACKGROUND OF THE INVENTION

A sensor system of the type mentioned at the outset is known from WO2004/023993 A1. Further sensor systems are known from EP 1 312 302 A2, DE 696 34 810 T2, DE 197 05 474 A1, DE 696 34 689 T2, U.S. Pat. No. 4,519,401 A and US 2003/0023146 A1.

An EEG cap with sensors is known from DE 102 15 115 A1, said sensors forming a sensor grid to form a measuring device in a mechanism for reactive automatic non-invasive controlled or regulated electromagnetic prevention of epileptic fits in vivo.

Brain parameter measurements take place, in particular, with the goal of clarifying the necessity for later therapy measures. An application example of this is a long term measurement of intracranial pressure for clarifying the question of whether a hydrocephalus patient requires a shunt valve and how a valve of this type has to be designed with regard to its dimensioning. Data collection of the intracranial pressure course over a relatively long time period, for example overnight or over several days is necessary for this in order to be able to derive a diagnosis from the dynamics of the intracranial pressure (ICP).

The use of the previously known sensor systems for processing questions of this type is very uncomfortable and cumbersome for the patient.

SUMMARY OF THE INVENTION

An object of the present invention is to develop a sensor system of the type mentioned at the outset in such a way that the use thereof remains comfortable for the patient even over a relatively long measuring period.

This object is achieved according to the invention by a sensor system comprising a head cap or a head hood, on which the receiving Unit is fixed to predetermine a relative positioning relative to the transmission unit.

It was recognised according to the invention that the components which are necessary to receive the measurement data from the implanted brain parameter sensor can be designed to be so light and compact that they can easily be fastened to a head cap or a head hood. The head cap or the head hood protects the receiving unit. The patient can move substantially freely with the head cap or the head hood, in other words does not have to be accommodated stationarily during the measuring period. The head cap or the head hood ensures an exact relative position of the receiving unit with respect to the transmission unit.

An antenna being part of a printed circuit is particularly light and compact and therefore comfortable to wear.

The receiving unit being fixed to the head cap or the head hood by a hook-and-loop connection allows a site-flexible relative positioning to adjust the receiving unit relative to the transmission unit. For this purpose, the receiving unit can be steplessly displaced relative to the head cap or the head hood until an intended desired signal strength is achieved in the transmission between the transmission unit and the receiving unit. It is possible, in particular, to make the axes of symmetry of the transmission unit and the receiving unit practically completely overlap one another, which ensures very good quality of the signal transmission.

A grid network head cap or head hood has proven successful in use in conjunction with EEG (electroencephalography) systems. A corresponding grid network head cap or head hood may also be used, after equipping with a corresponding receiving unit, in the sensor system, in which the head cap or the head hood has a plurality of individual bands or individual tubes, which predetermine a grid network, wherein the receiving unit can be fixed on crossing points of the grid network.

A housing ring by means of which the receiving unit can be placed on a patient's head ensures that the receiving unit rests securely on a patient's head. As the transmission unit is generally accommodated between the scalp and the cranium, the transmission unit is a clearly feelable elevation on the patient's head. The housing ring is preferably dimensioned such that it surrounds this elevation at least in portions and this improves the relative positioning of the transmission unit with respect to the receiving unit.

Only some of the components forming the receiving unit can be accommodated in the housing or housing ring which can be placed on the patient's head. Preferably only the antenna of the receiving unit is accommodated in the housing or housing ring, whereas the other components of the receiving unit are connected to the antenna, for example, by means of a cable-bound or else a cableless signal connection. The component which can be placed on the patient's head can then be configured in a light and compact manner.

Configurations comprising a flexible membrane, by means of which the receiving unit can be placed on the patient's head, and wherein a layer of variable shape, in particular a gel layer, is arranged between the flexible membrane and the antenna improve the placing of the receiving unit on the transmission unit and therefore the relative positioning of these two units.

An integration wherein the data read module and the receiving unit are configured as an integral modular unit and can be fixed to the head cap or the head hood avoids, in particular, the patient having to also carry additional components, for example on the belt, in addition to the head cap or the head hood.

The advantages of a head cap or a head hood with a receiving unit for use in a sensor system according to the invention correspond to those which were already stated above with reference to the sensor system according to the invention.

An embodiment of the invention will be described in more detail below with the aid of the drawings.

DESCRIPTION OF THE PREFERRED EMBODIMENT

Figure 1:
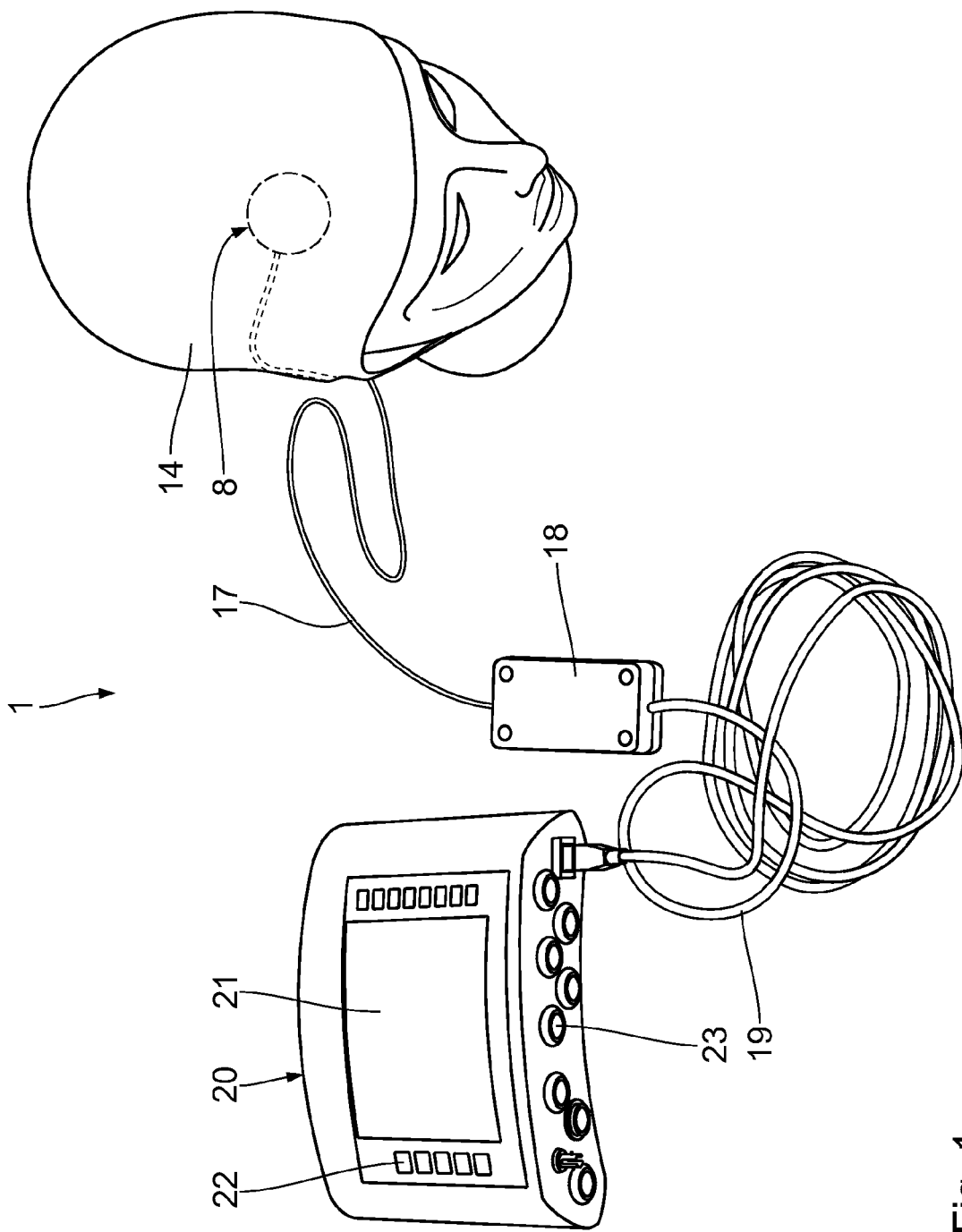
FIG. 1 shows a sensor system for measuring, transmitting, processing and displaying a brain parameter.

A sensor system 1 shown as a whole in FIG. 1 is used to measure, transmit, process and display a brain parameter, in particular an intracranial pressure.

Figure 2:
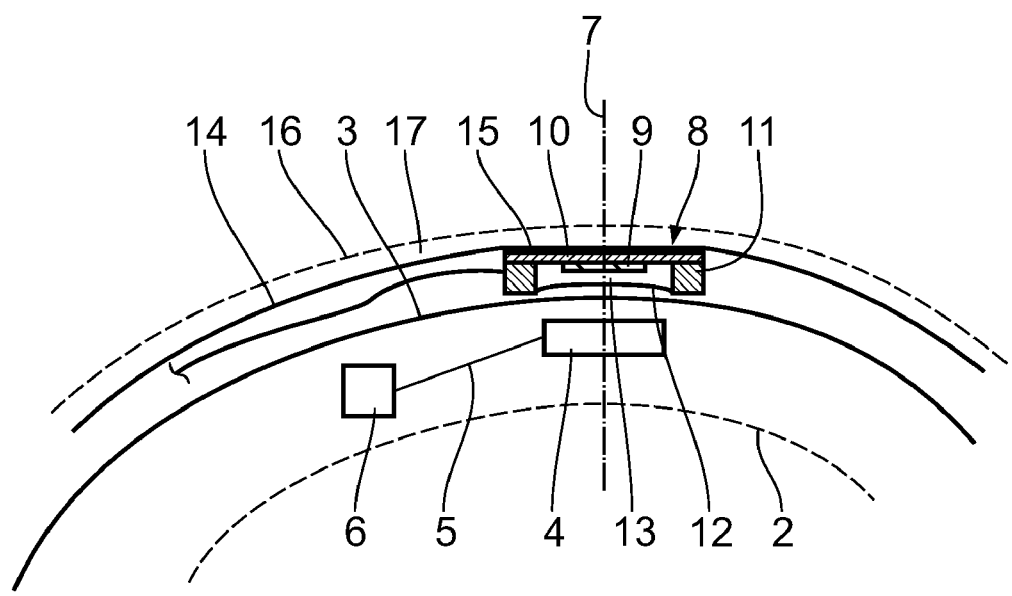
FIG. 2 schematically shows a section through a head cap or a head hood of the sensor system placed on a patient's head in the region of an antenna fixed to the head cap or the head hood.
Figure 3:
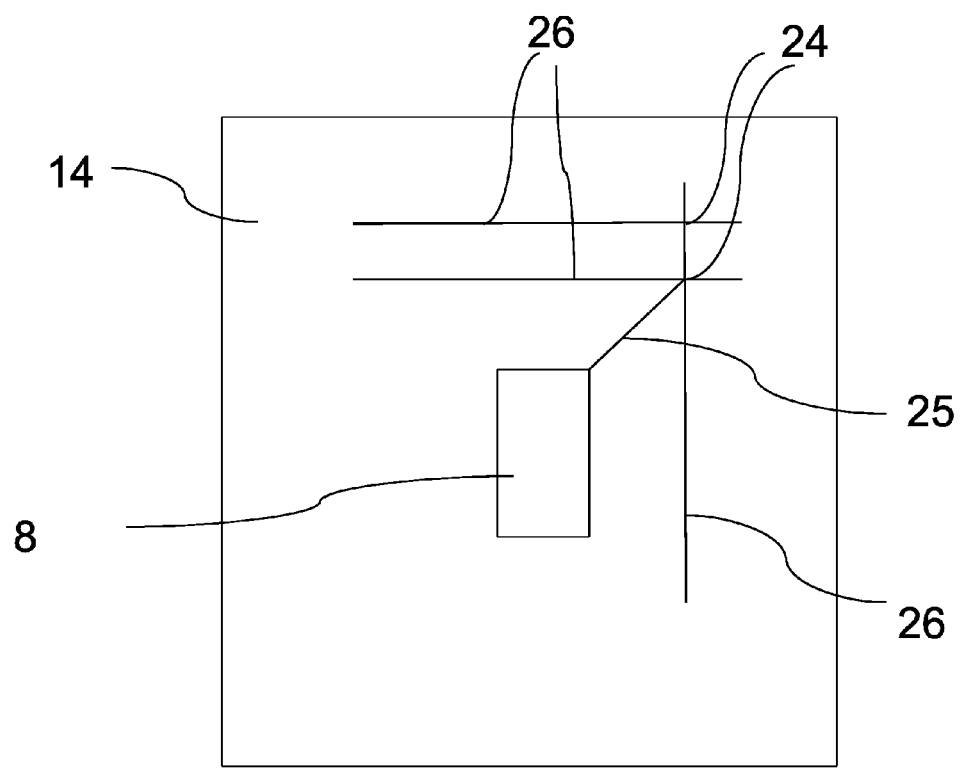
FIG. 3 schematically shows an embodiment in which the head cap is configured as a network of a plurality of individual bands or individual tubes.

The sensor system 1 includes a brain parameter sensor, which is not shown in more detail and can be implanted in a patient's head. The cutout-wise cross section of FIG. 2 shows components of the implanted brain parameter sensor, which are arranged between a cranium 2 indicated by a dashed lines in FIG. 2 and the scalp 3 of a patient. A wireless sensor transponder 4 with an antenna coil belongs to this. The sensor transponder 4 is also designated a transmission unit below. The transmission unit 4 is in electrical contact by means of a line 5 and a rectifier, not shown, with a capacitor 6. The view according to FIG. 2 is extremely schematic and not true to scale.

The sensor transponder 4 does not have its own energy source. The sensor transponder 4 additionally has an analogue to digital converter, not shown in more detail. This is used to digitise the sensor measurement data to be passed on from the sensor transponder 4.

An axis 7 of rotational symmetry of the antenna coil of the transmission unit 4 is shown by dashed lines in FIG. 2. The axis 7, due to the arrangement of the transmission unit 4, runs substantially normal to the outer wall of the cranium 2 in the region where the antenna coil of the transmission unit 4 rests thereon.

The transmission unit 4 is connected to sensor element of the brain parameter sensor, by means of a signal connection, not shown. The sensor element is, for example, configured as a catheter guided through the cranium 2 with a pressure measurement head.

Associated with the transmission unit 4 is an outer transceiver unit 8 of the sensor system 1, which will also only be called a receiving unit or a reader below. The receiving unit 8 is arranged outside the patient's head. The receiving unit 8 has an antenna 9, which is wirelessly in signal connection with the transmission unit 4 for the supply of energy and for data transmission. The antenna 9 is printed as part of a printed circuit (PCB, printed circuit board) on a thin board 10 with a thickness of between 0.8 mm and 1.5 mm. An even thinner board is also possible. To improve the adaptability of the receiving unit 8, the board 10 may be configured as flexible, in other words a bendable board. The antenna 9 also has the shape of a coil, the axis of rotational symmetry coinciding with the axis 7. The coil windings of the units 4, 8 may, in particular, be arranged helically.

The board 10 is fastened to an annular housing 11 with a diameter of a few cm. The axis of rotational symmetry of the housing 11 also coincides with the axis 7. The site of fastening of the board 10 is on a side of the housing 11 remote from the scalp 3.

A flexible membrane 12 is also fixed to the housing 11 on the side facing the scalp 3. The membrane 12 thus lies between the antenna 9 and the scalp 3.

Arranged between the antenna 9 and the membrane 12 is a layer 13 of a resilient material of variable shape, in particular made of a flowable and highly viscous material, in particular made of a gel.

When placing the receiving unit 8 via the housing 11 on the scalp 3 in the region of the transmission unit 4, the membrane 12, because of a targeted displacement of the layer 13, adapts to the shape of the patient's head at this point, so a correct seat of the receiving unit 8 relative to the transmission unit 4 is ensured.

The receiving unit 8 is fixed on the inside of a head cap or a head hood 14, which is also part of the sensor system 1. A hook-and-loop connection with a hook-and-loop band 15 which is stuck on the side facing the head cap or the head hood 14 on the housing 11 and the board 10 of the receiving unit 8, is used to fasten the receiving unit 8 on the head cap or the head hood 14. The receiving unit 8 can be applied at any point on the inside of the head cap or the head hood 14 by means of this hook-and-loop connection, so a desired relative positioning of the receiving unit 8 with respect to the transmission unit 4 is possible. The head cap or the head hood 14 is made of an expandable gauze or cotton material closely adjacent to the patient's head. The head cap or the head hood 14 is adapted in section to the shape of the patient's head. The head cap or the head hood 14, for fixing to the patient's head, may have a chin band, not shown in the drawing. In addition to the head cap or the head hood 14, an outer overcap or overhood 16 indicated by dashed lines in FIG. 2 may also be provided, which absorbs forces from the outside and therefore secures the then inner head cap or head hood 14 against undesired slipping relative to the cranium 2.

The antenna 9 of the receiving unit 8 is in signal connection with a data read module 18 by means of a signal cable 17, which extends in portions between the scalp 4 and the head cap or the head hood 14. The data read module 18 comprises a control unit for controlling the implanted brain parameter sensor by means of the receiving unit 8, by means of which a bidirectional data transmission is possible. Furthermore, the data read module 18 has a high frequency source for generating a carrier frequency of 13.56 MHz. The data read module 18 additionally has a signal memory. The data read module 18 approximately has the size of a cigarette packet and can be carried by the patient on the belt.

The data read module 18 is in signal connection by means of a further signal cable 19 with a data processing and display device 20. The latter has a display 21 and a plurality of operating buttons 22 and connection ports 23, in particular at least one USB interface. The data processing and display device 20 can be connected to an external voltage source. As an alternative or in addition, the data processing and display device 20 may have an internal energy source, for example in the form of battery or a chargeable accumulator. The data read module 18, the receiving unit 8 and, wirelessly during a measurement process, also the transmission unit 4 are supplied by means of this energy source.

The signal connection between the antenna 9 and the data read module 18, on the one hand, and the data read module 18 and the data processing and display device 20, on the other hand, may be a USB interface or else an RS232 interface, in other words a digital interface.

A brain parameter measuring process, which is regularly repeated over a relatively long time period, for example over the course of several days, proceeds as follows:

The data read module 18 firstly sends by means of the receiving unit 8 an HF signal to the transmission unit 4. The HF signal is rectified and charges the capacitor 6 for the temporary energy supply of the transmission unit 4. After this charging process, the HF signal is deactivated.

The brain parameter sensor, supplied by means of the capacitor 6, then records the brain parameter measurement signal, for example an intracranial pressure value. The HF signal is then activated again and the transmission unit 4, with the HF signal as the carrier frequency, sends the measurement value digitised by means of the analogue to digital converter as a digitally modulated signal to the receiving unit 8. A conversion or decoding of the modulated HF signal into a digital PC-compatible signal takes place in the receiving unit 8. Depending on the interface standard used in the sensor system 1, this may, for example, be a USB or an RS232 signal. This converted measurement signal is transmitted to the data read module 18 by means of the signal cable 17. The transmitted signal is then transmitted by the signal cable 19 to the data processing and display device 20 for further processing and display.

Instead of a gauze or cotton configuration of the head cap or the head hood 14 and optionally the overcap or overhood 16, the head cap or the head hood 14 may also be configured as a network of a plurality of individual bands or individual tubes. A grid network is then predetermined by these individual bands or individual tubes. The receiving unit 8 may then have fastening means 25 on the individual bands or individual tubes 26 which, in particular, allow the receiving unit 8 to be fastened to crossing points 24 of this grid network. Corresponding embodiments of head caps or head hoods of individual bands or individual tubes are known in conjunction with EEG head caps or head hoods.

In a further variant of the sensor system 1, the receiving unit 8 and the data read module 18 are configured as an integrated modular unit and fastened to the head cap or the head hood 14. For the weight distribution of this integrated modular unit, the data read module can also be fastened separately from the receiving unit 8 on the inside of the head cap or the head hood 14, for example at a position opposing the receiving unit 8. The receiving unit 8 and the date read module 18 may then be connected to one another by means of a short signal cable.

A corresponding integration of the receiving unit 8 is also possible with individual components of the data read module 18, for example with the HF source or with the control unit of the data read module 18. The remaining components are then in turn connected by means of a signal connection to an external module, in other words a module provided outside the head cap or the head hood 14.

In these integrated variants, in which the receiving unit 8 also has additional components of the data read module 18, it is also possible for the receiving unit 8 to have its own energy supply, for example in the form of a button cell. In this case, a cable-bound signal connection may also be dispensed with and, instead of the signal cable 17, a wireless signal connection, for example a Bluetooth signal connection, may be used.

In a further variant of the sensor system 1, the data read module 18 has its own energy supply and, instead of a cable-bound signal connection to the data processing and display device 20 (signal cable 19), a wireless signal connection is present, which can also be implemented, for example, by means of a Bluetooth connection.

The data processing and display device 20 does not have to be constantly in signal connection with the data read module 18. It is sufficient if the data processing and display device 20 reads the recorded measurement data from the data read module 18 on completion of the measuring time, for example lasting several days. A corresponding data connection is necessary only then, so the patient only has to wear the head cap or the head hood 14 with the receiving unit 8 and the data read module 18 during the measuring time.

The site-flexible positioning of the receiving unit 8 by means of the hook and-loop connection with the hook-and-loop band 15 allows an exact orientation of the receiving unit 8 with respect to the transmission unit 4, so the coil axes of these two units 4, 8 coincide. This ensures an optimal signal transmission between the units 4 and 8.

In an embodiment, not shown in more detail, the receiving unit 8 is configured with an annular housing 11, in which an also annular antenna 9 is incorporated. This ring antenna in this embodiment is placed on the head of the patient. The remaining receiving unit, in other words the further components, which in the embodiment according to FIGS. 1 and 2 are configured, in particular, on the printed circuit on the board 10, are connected to the ring antenna by means of a data cable. This remaining receiving unit may be carried, for example on the belt or placed on a laboratory table. This separation of the ring antenna from the other receiving unit reduces the overall size and the weight of the component to be placed on the head of the patient.

The housing of the ring antenna of this embodiment, not shown further, may have characteristic bulges and/or troughs and/or other indentations, which are used, when manually placing the ring antenna, to facilitate the positioning thereof. For example, three bulges and/or troughs and/or indentations may be present, which are arranged approximately equally distributed on the outer periphery of the ring antenna.

The housing of the ring antenna may have radially extending indentations on the upper side of the ring antenna remote from the patient's head in the placed-on position. These radially extending indentations may be used as fastening aids for a hook-and-loop band for fixing the ring antenna to the head cap or the head hood 14.

The invention claimed is:

1. A senor system (1) for measuring, transmitting, processing and displaying a brain parameter
   with at least one implantable brain parameter sensor with a wireless transmission unit (4) for measuring the brain parameter,
   with at least one receiving unit (8) with an antenna (9), which is in wireless signal connection with the transmission unit (4),
   with at least one data read module (18), which is in signal connection with the antenna (9) by means of a signal connection (17),
   with at least one data processing and display device (20), which is in signal connection (19) with the data read module (18),
   comprising a head cap or a head hood (14) configured to be worn on a patient's head, outside of the patient's scalp, on which the receiving unit (8) is fixed to predetermine a relative positioning relative to the transmission unit (4), and
   wherein the head cap or the head hood (14) has a plurality of at least one of individual bands or individual tubes, which are configured as a grid network having a plurality of crossing points, wherein the receiving unit (8) can be fixed on at least one of the plurality of crossing points of the grid network.

2. A sensor system (1) according to claim 1, wherein the antenna (9) is part of a printed circuit.

3. A sensor system (1) according to claim 1, wherein the receiving unit (8) is fixed to head cap or the head hood (14) by a hook-and-loop connection (15).

4. A sensor system (1) according to claim 1, wherein the receiving unit (8) can be placed by means of a housing ring (11) on a patient's head.

5. A sensor system (1) according to claim 1, comprising a flexible membrane (12), by means of which the receiving unit (8) can be placed on the patient's head.

6. A sensor system (1) according to claim 5, wherein a layer (13) of variable shape is arranged between the flexible membrane (12) and the antenna (9).

7. A sensor system (1) according to claim 6, wherein the layer (13) is a gel layer.

8. A sensor system (1) according to claim 1, wherein the data read module (18) and the receiving unit (8) are configured as an integral modular unit and can be fixed to the head cap or the head hood (14).

9. A head cap or head hood (14) comprising the at least one receiving unit (8) of the sensor system (1) according to claim 1, the head cap or head hood formed of a flexible material.

10. A sensor system (1) according to claim 1, wherein the receiving unit (8) has fastening means to allow the receiving unit be fastened to crossing points of said grid network.

* * * * *